United States Patent [19]

Koga et al.

[11] Patent Number: 4,816,479
[45] Date of Patent: Mar. 28, 1989

[54] XANTHONE DERIVATIVES AND PROCESS FOR PRODUCING THE SAME

[75] Inventors: Hiroshi Koga, Saitama; Takashi Mori; Takashi Dan, both of Tokyo; Michitaka Akima, Saitama, all of Japan

[73] Assignee: Chugai Seiyaku Kabushiki Kaisha, Tokyo, Japan

[21] Appl. No.: 937,101

[22] Filed: Dec. 2, 1986

Related U.S. Application Data

[62] Division of Ser. No. 775,240, Sep. 12, 1985, Pat. No. 4,661,607.

[30] Foreign Application Priority Data

Sep. 21, 1984 [JP] Japan ..................... 59-196796
Sep. 28, 1984 [JP] Japan ..................... 59-204351

[51] Int. Cl.$^4$ ..................... A61K 31/35; C07D 311/86
[52] U.S. Cl. ..................... 514/455; 549/392; 514/869
[58] Field of Search ............... 549/391, 392; 514/455, 514/869

[56] References Cited

U.S. PATENT DOCUMENTS 3,758,506  9/1973  Godfroid et al. ............... 514/869 X

FOREIGN PATENT DOCUMENTS 923132   4/1963  Fed. Rep. of Germany.
1172271  6/1964  Fed. Rep. of Germany.
1417961 10/1965  France ..................... 549/392
0392552 10/1965  Switzerland ..................... 549/392
2065107  6/1981  United Kingdom.

OTHER PUBLICATIONS

Coffey, Rodd's Chemistry of Carbon Compounds, 2nd ed., vol. IV, pp. 316–335 (1977).
Mainkur. Chem. Abs. 59, 9994a–c (1963).
Chemical Abstracts, vol. 72, No. 11, Mar. 16, 1970, p. 396, column 1, Abstract No. 55161v, Columbus, Ohio, U.S.; Puranik et al: "Furano Compounds IV", & INdian J. of Appl. Chem. 1968, 31(3–4), 105–107.
Chemical Abstracts, vol. 57, No. 10, Nov. 12, 1962, columns 11979a–11980a, Columbus, Ohio, U.S.; F. Scheinmann "Xanthone series V. Infrared spectra of substituted and extended xanthones", & Tetrahedron, 1962, 18, 853–858.
Shutske et al., "[(3-Aryl-1,2-benzisoxazol-6-61)oxy]acetic Acids. A new Diuretic Series", J. Med. Chem., 1982, 25, pp. 36–44.
Platner et al., "Substituted 5,6-Dihydrofuro[3,2-f]-1,-2-benzisoxazole-6-carboxylic Acids; High-Ceiling Diuretics with Uricosuric Activity", J. Med. Chem., 1984, 27, pp. 1016–1026.

Primary Examiner—John W. Rollins
Assistant Examiner—W. Catchpole
Attorney, Agent, or Firm—Browdy and Neimark

[57] ABSTRACT

Xanthone derivatives of the formula (I):

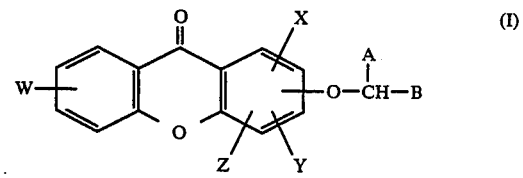

wherein W, X, Y and Z which may be the same or different represent a hydrogen atom, a halogen atom or a lower alkyl group having 1 to 4 carbon atoms; A is a hydrogen atom B is a hydroxymethyl group, a lower alkoxycarbonyl group having 1 to 4 carbon atoms, or a carboxyl group, provided that a —O—CH$_2$—B group is bonded to the 2- or 3-position of the xanthone ring and that there is no case in which X, Y, and Z are each a hydrogen atom concurrently; as well as intoxic salts thereof when B is a carboxyl group, and a process for preparing the same are disclosed.

The compounds of formula (I) in accordance with the present invention are useful as diuretics having uricosuric activity and can be used in the treatment of edema or hypertension.

9 Claims, No Drawings

XANTHONE DERIVATIVES AND PROCESS FOR PRODUCING THE SAME

This is a division of application Ser. No. 775,240, filed Sept. 12, 1985, now U.S. Pat. No. 4,661,607.

FIELD OF THE INVENTION

The present invention relates to xanthone derivatives of the formula (I):

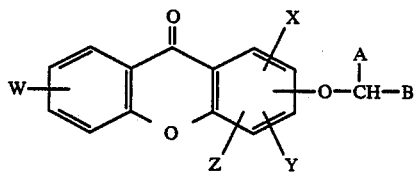

(wherein W, X, Y and Z which may be the same or different represent a hydrogen atom, a halogen atom or a lower alkyl group having 1 to 4 carbon atoms; A is a hydrogen atom or may bind to X or Y to form a cyclic methylene chain; B is a hydroxymethyl group, a lower alkoxycarbonyl group having 1 to 4 carbon atoms, or a carboxyl group, provided that W is neither a hydrogen atom nor a 7-position methyl group when X, Y and Z are each a hydrogen atom, and A is a hydrogen atom and B is a carboxyl group or a lower alkoxycarbonyl group), as well as intoxic salts thereof when B is a carboxyl group.

The compounds of formula (I) in accordance with the present invention are useful as diuretics having uricosuric activity and can be used in the treatment of edema or hypertension.

BACKGROUND OF THE INVENTION

Diuretics known to have uricosuric activity like the compounds of the present invention are phenoxyacetic acids typified by thienylic acid (U.S. Pat. No. 3,758,506).

Conventional diuretic hypotensive agents are extensively used as drugs of the first choice in the treatment of hypertension, but they have a high potential of causing hyperuricemia as a side effect. Furthermore, hypertension is often complicated by hyperuricemia and many cases of hyperuricemia are believed to be caused by disorders in the excretion of uric acid. Under these circumstances, there exists a strong need in medical fields for the development of diruetics having uricosuric activity. As already mentioned, thienylic acid is known to be a potential diuretic having uricosuric activity, but is yet to be commercialized because of the high possibility of causing liver disorders as a side effect.

SUMMARY OF THE INVENTION

As a result of various studies made to overcome these disadvantages, the present inventors have found that the xanthone derivatives of formula (I) have both uricosuric and diuretic activities and yet cause minimum side effects on the liver. The present invention has been accomplished on the basis of this finding.

The xanthone derivatives of formula (I) in accordance with the present invention are specifically classified as the compounds of formula (II) and furoxanthones of formula (III):

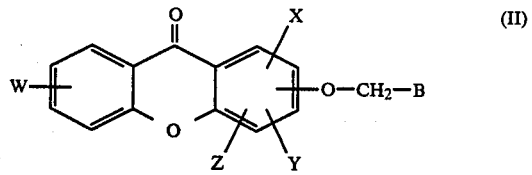

(wherein W, X, Y, Z and B mean the same as defined for formula (I), provided that W is neither a hydrogen atom nor a 7-position methyl group when X, Y, Z are each a hydrogen atom and B is a carboxyl group or a lower alkoxycarbonyl group);

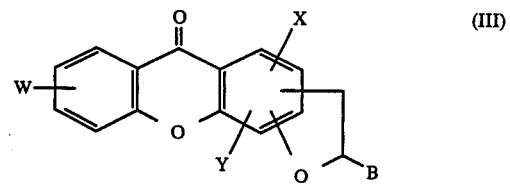

(wherein W, X, Y and B mean the same as defined above).

In the xanthone derivatives of formulas (I), (II) and (III), the halogen atom is fluorine, chlorine, bromine or iodine, and the lower alkyl group is a straight-chained or branched alkyl group having 1 to 4 carbon atoms). When B is a carboxyl group, the derivatives may form salts with bases. Illustrative salts include alkali metal salts, alkaline earth metal salts and substituted or unsubstituted amine salts. Specific examples of such salts are sodium salts, calcium salts, magnesium salts, ammonium salts, lower alkylamine salts and ethanolamine salts. These salts may be readily formed by conventional methods.

The compounds of formula (I) in accordance with the present invention are novel. The compounds of formula (II) may be prepared by reacting compounds of formula (IV):

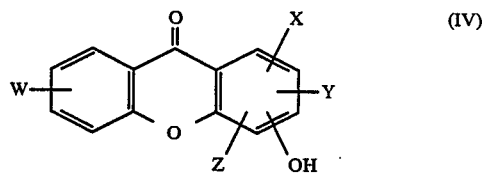

(wherein W, X, Y and Z mean the same as defined above) with compounds of the formula: L—CH$_2$—B (wherein B is the same as defined above, and L is a halogen atom, a hydroxyl group or an acyloxy group as a leaving group). The reaction is preferably performed in the presence of a base in an inert solvent. Examples of the inert solvent include ethers, alcohols, hydrocarbons, aromatic hydrocarbons, water, and aprotic polar solvents such as N,N-dimethylformamide and dimethyl sulfoxide. Illustrative bases are hydrides, alkoxides, hydroxides and carbonates of alkali metals and organic bases. More specific examples include sodium hydride, sodium methoxide, sodium ethoxide, sodium hydroxide, potassium hydroxide, sodium carbonate, potassium carbonate and triethylamine. The reaction temperature is appropriately selected from the range of 0° C. to about 150° C.

The xanthone derivatives of formula (II) wherein B is a carboxyl group may also be prepared from corresponding compounds wherein B is a lower alkoxycarbonyl group by conventional methods, for example, by the hydrolysis of them using alkaline hydroxides.

Specific examples of the furoxanthone derivatives of formula (III) in accordance with the present invention are 5-oxo-5H-furo[3,2-b]xanthenes and 6-oxo-6H-furo[2,3-c]xanthenes. Compounds of formula (IIIa) represented by the following formula are included within the scope of the compounds of the present invention.

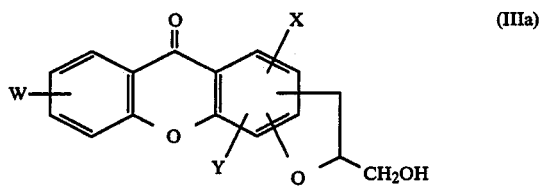

(wherein X, Y and W are the same as defined above) They may be prepared by reacting peracids with compounds of formula (V):

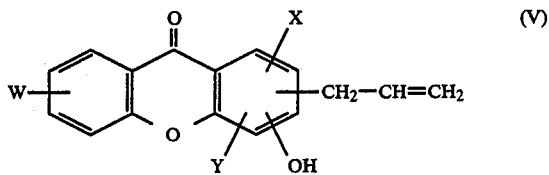

(wherein X, Y and W mean the same as defined above, provided that the hydroxyl and allyl groups are substituted at vicinal positions).

By subjecting these compounds of formula (IIIa) to oxidation, compounds of formula (IIIb) which are also within the scope of the invention are obtained:

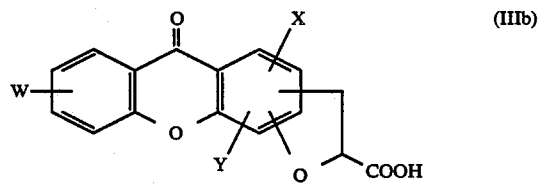

(wherein X, Y and W are the same as defined above).

The compounds of formula (III) wherein B is a lower alkoxycarbonyl group may be prepared by esterifying the compounds of formula (IIIb) in accordance with conventional methods. In these productions, the reaction is carried out in an inert solvent such as ethers and hydrocarbons. The reaction temperature is properly selected from the range of 0° C. to about 150° C. Organic peracids such as peracetic acid, perbenzoic acid and m-chloroperbenzoic acid may be used as peracids in the step of producing the compounds of formula (IIIa) from the compounds of formula (V). The oxidative reaction by which the compounds of formual (IIIa) are converted to the compounds of formula (IIIb) may be performed by a conventional technique, such as by using oxides of manganese, chromium, etc. The compounds of formula (V) may be prepared by subjecting the corresponding allyl aryl ethers to the Claisen rearrangement reaction.

PHARMACOLOGICAL ACTIVITIES OF THE COMPOUNDS

The diuretic and uricosuric activities of the compounds of the present invention were confirmed by the following experiment.

Method:

Seven-week old Wistar-Imamichi rats that had been starved for 24 hours were divided in groups of four or five heads so that the animals of each group would excrete almost the same amount of urine. After forced urination, the rats were orally administered the test compounds that were suspended in physiological saline containing 3% gum arabic in a dose volume of 25 ml per kg of the body weight. The suspensions were administered typically in an amount of 100 mg/kg. Control rats were given only physiological saline containing 3% gum arabic. The animals were housed in separate metabolic cages and the urine excreted from each animal was collected over a period of 6 hours following the administration of the test compounds of physiological saline after completion starvation. The urine volume was directly read on a measuring cylinder after forced urination thereinto, and the amount of urine per kg of the body weight was calculated. The amount of uric acid excreted in the urine was determined by the uricase-catalase method.

Results:

As is apparent from the following table, the compounds of the present invention exhibited significant levels of diuretic and uricosuric activities, which were found to be long-lasting and dose-dependent. The compound numbers given in the table are keyed to the specific Examples shown later in this specification.

TABLE

| Test compound | Amount of urine | | Amount of uric acid | |
|---|---|---|---|---|
| | ml/kg | % | ml/kg | % |
| Control group | 17.7 ± 3.9 | 100 | 3.44 ± 0.57 | 100 |
| Compound 13 | 35.4 ± 7.6 | 199.5[c] | 5.11 ± 1.00 | 148.6[c] |
| Control group | 16.7 ± 6.9 | 100 | 3.05 ± 0.48 | 100 |
| Compound 21 | 31.8 ± 6.6 | 190.8[c] | 3.86 ± 0.61 | 126.3[b] |
| Control group | 14.7 ± 1.8 | 100 | 2.38 ± 0.23 | 100 |
| Compound 23 | 36.9 ± 3.3 | 250.3[c] | 3.13 ± 0.22 | 131.7[a] |
| Control group | 18.1 ± 2.1 | 100 | 3.43 ± 0.20 | 100 |
| Compound 35 | 49.7 ± 2.0 | 275.0[c] | 4.30 ± 0.22 | 125.2[a] |

[a] $P < 0.05$
[b] $P < 0.01$,
[c] $P < 0.001$

DETAILED DESCRIPTION OF THE INVENTION

The following examples are provided for further illustrating the claimed compounds but are not to be construed as limiting the invention.

EXAMPLE 1

A mixture of 2.6 g of 4-chloro-8-fluoro-3-hydroxy-9-oxo-9H-xanthene, 2.8 g of postassium carbonate, 3.3. g of ethyl bromoacetate and 40 ml of N,N-dimethylformamide (DMF) was stirred at 60°–70° C. for 4 hours. After cooling the mixture, water was added thereto and the resulting crystal was recovered by filtration, washed with water and dried. Recrystallization from ethanol gave 3.4 g of ethyl 4-chloro-8-fluoro-9-oxo-9H-xanthene-3-yloxyacetate. A mixture of this ester (3.3 g), sodium hydroxide (1.9 g) and water (100 ml) was refluxed for 30 minutes. After cooling, the mixture was rendered acidic with concentrated hydrochloric acid and the resulting crystal was recovered by filtration and dried. Recrystallization from DMF gave 2.5 g of 4-chloro-8-fluoro-9-oxo-9H-xanthene-3-yloxyacetic acid. m.p. 300° C.

This compound exhibited a mass spectrum having a molecular ion peak at m/e 322.

EXAMPLE 2

A mixture of 1.2 g of 4-chloro-3-hydroxy-9-oxo-9H-xanthene, 1.7 g of postassium carbonate, 2.1 g of ethyl bromoacetate and 30 ml of DMF was stirred at 60°–70° C. for 3 hours. After cooling the mixture, water was added and the resulting crystal was recovered by filtration, washed with water and dried. Recrystallization from ethanol gave 1.1 g of ethyl 4-chloro-9-oxo-9H-xanthene-3-yloxyacetate. m.p. 183°–185° C.

A mixture of this ester (0.9 g), sodium hydroxide (0.7 g) and water (40 ml) was refluxed for 1 hour. After cooling, the mixture was rendered acidic with hydrochloric acid and the solid crystal was recovered by filtration, washed with water and dried. Recrystallization from ethanol gave 0.7 g of 4-chloro-9-oxo-9H-xanthene-3-yloxyacetic acid. m.p. 280°–281° C.

This compound exhibited a mass spectrum having a molecular ion peak at m/e 304.

EXAMPLE 3

A mixture of 1.0 g of 3-hydroxy-4-methyl-9-oxo-9H-xanthene, 1.5 g of potassium carbonate, 1.8 g of ethyl bromoacetate and 20 ml of DMF was agitated at 60°–70° C. for 2 hours. After cooling the mixture, 2 g of sodium hydroxide and 40 ml of water were added, and the resulting mixture was stirred at 90°–100° C. for 30 minutes. After cooling, the mixture was rendered acidic with hydrochloric acid and the solid crystal was recovered by filtration, washed with water and dried. Recrystallization from ethanol gave 1.0 g of 4-methyl-9-oxo-9H-xanthene-3-yloxyacetic acid. m.p. 244°–247° C. This compound gave a mass spectrum having a molecular ion peak at m/e 284.

EXAMPLE 4

A mixture of 1.8 g of 8-fluoro-3-hydroxy-9-oxo-9H-xanthene, 3.2 g of potassium carbonate, 3.7 g of ethyl bromoacetate and 100 ml of DMF was stirred at 60°–70° C. for 4 hours. After cooling the mixture, 5 g of sodium hydroxide and 100 ml of water were added, and the resulting mixture was stirred at 90°–100° C. for 30 minutes. After cooling, the mixture was rendered acidic with hydrochloric acid and the solid crystal was recovered by filtration, washed with water and dried. Recrystallization from ethanol gave 2.0 g of 8-fluoro-9-oxo-9H-xanthene-3-yloxyacetic acid. m.p. 180°–183° C. This compound showed a mass spectrum having a molecular ion peak at m/e 288.

EXAMPLE 5

A mixture of 1.5 g of 8-fluoro-3-hydroxy-4-methyl-9-oxo-9H-xanthene, 3.0 g of potassium carbonate, 3.6 g of ethyl bromoacetic and 40 ml of DMF was stirred at 60°–70° C. for 2 hours. After cooling the mixture, sodium hydroxide (3 g) and water (40 ml) were added and the resulting mixture was stirred at 90°–100° C. for 30 minutes. After cooling, the mixture was rendered acidic with hydrochloric acid and the solid crystal was recovered by filtration, washed with water and dried. Recrystallization from DMF gave 1.4 g of 8-fluoro-4-methyl-9-oxo-9H-xanthene-3-yloxyacetic acid. m.p. 259°–261° C.

This compound showed a mass spectrum having a molecular ion peak at m/e 302.

EXAMPLE 6

A mixture of 1.3 g of 2-chloro-8-fluoro-3-hydroxy-9-oxo-9H-xanthene, 1.7 g of postassium carbonate, 2.1 g of ethyl bromoacetate and 30 ml of DMF was stirred at 60°–65° C. for 3 hours. After cooling the mixture, 2 g of sodium hydroxide and 100 ml of water were added and the resulting mixture was stirred at 90°–100° C. for 30 minutes. After cooling, the mixture was rendered acidic with hydrochloric acid and the solid crystal was recovered by filtration, washed with water and dried. Recrystallization from DMF gave 1.0 g of 2-chloro-8-fluoro-9-oxo-9H-xanthene-3-yloxyacetic acid. m.p. 239°–242° C. This compound gave a mass spectrum having a molecular ion peak at m/e 322.

EXAMPLE 7

A mixture of 2.6 g of 3-chloro-8-fluoro-2-hydroxy-9-oxo-9H-xanthene, 3.4 g of potassium carbonate, 4.2 g of ethyl bromoacetate and 60 ml of DMF was stirred at 60°–65° C. for 5 hours. After cooling the mixture, 4 g of sodium hydroxide and 100 ml of water were added and the resulting mixture was stirred at 90°–100° C. for 30 minutes. After cooling, the mixture was rendered acidic with hydrochloric acid and the solid crystal was recovered by filtration, washed with water and dried. Recrystallization from ethanol gave 1.2 g of 3-chloro-8-fluoro-9-oxo-9H-xanthene-2-yloxyacetic acid. m.p. 242°–245° C. This compound exhibited a mass spectrum having a molecular ion peak at m/e 322.

EXAMPLE 8

A mixture of 4,8-dichloro-3-hydroxy-9-oxo-9H-xanthene (2.8 g), potassium carbonate (3.4 g), ethyl bromoacetate (4.2 g) and DMF (60 ml) was stirred at 60°–65° C. for 6.5 hours. After cooling the mixture, sodium hydroxide (4 g) and water (100 ml) were added and the solid crystal was recovered by filtration, washed with water and dried. Recrystallization from DMF gave 2.4 g of 4,8-dichloro-9-oxo-9H-xanthene-3-yloxyacetic acid. m.p. 270°–271° C. This compound showed a mass spectrum having a molecular ion peak at m/e 338.

EXAMPLE 9

A mixture of 4,6-dichloro-3-hydroxy-9-oxo-9H-xanthene (2.0 g), potassium carbonate (3.4 g), ethyl bromoacetate (4.2 g) and DMF (60 ml) was stirred at 60°–65° C. for 4 hours. After cooling the mixture, sodium hydroxide (4 g) and water (100 ml) were added and the resulting mixture was stirred at 90°–100° C. for 30 minutes. After cooling, the mixture was rendered acidic with hydrochloric acid and the solid crystal was recovered by filtration, washed with water and dried. Recrystallization from DMF gave 1.5 g of 4,6-dichloro-9-oxo-9H-xanthene-3-yloxyacetic acid. m.p. 270° C. This compound gave a mass spectrum having a molecular ion peak at m/e 338.

EXAMPLE 10

A mixture of 4-bromo-8-fluoro-2-hydroxy-9-oxo-9H-xanthene (1.5 g), potassium carbonate (3.4 g), ethyl bromoacetate (4.2 g) and DMF (60 ml) was stirred at 60°–65° C. for 4 hours. After cooling the mixture, sodium hydroxide (2 g) and water (100 ml) were added and the resulting mixture was stirred at 90°–100° C. for 30 minutes. After cooling, the mixture was rendered acidic with hydrochloric acid and the solid crystal was recovered by filtration, washed with water and dried. Recrystallization from ethanol gave 1.2 g of 4-bromo-8-fluoro-9-oxo-9H-xanthene-2-yloxyacetic acid. m.p. 220°–223° C. This compound gave a mass spectrum having a molecular ion peak at m/e 366.

EXAMPLE 11

A mixture of 4,7-dichloro-3-hydroxy-9-oxo-9H-xanthene (2.0 g), potassium carbonate (3.4 g), ethyl bromoacetate (4.2 g) and DMF (60 ml) was stirred at 60°–65° C. for 4 hours. After cooling the mixture, sodium hydroxide (4 g) and water (100 ml) were added and the resulting mixture was stirred at 90°–100° C. for 30 minutes. After cooling, the mixture was rendered acidic with hydrochloric acid and the solid crystal was recovered by filtration, washed with water and dried. Recrystallization from DMF gave 1.3 g of 4,7-dichloro-9-oxo-9H-xanthene-3-yloxyacetic acid. m.p. 262°–263° C. This compound gave a mass spectrum having a molecular ion peak at m/e 338.

EXAMPLE 12

A mixture of 4,5-dichloro-3-hydroxy-9-oxo-9H-xanghene (2.0 g), potassium carbonate (3.4 g), ethyl bromoacetate (4.2 g) and DMF (60 ml) was stirred at 60°–65° C. for 4 hours. After cooling the mixture, sodium hydroxide (4 g) and water (100 ml) were added and the resulting mixture was stirred at 90°–100° C. for 30 minutes. After cooling, the mixture was rendered acidic with hydrochloric acid and the solid crystal was recovered by filtration, washed with water and dried. Recrystallization from DMF gave 1.5 g of 4,5-dichloro-9-oxo-9H-xanthene-3-yloxyacetic acid. m.p. 283°–286° C. This compound gave a mass spectrum having a molecular ion peak at m/e 338.

EXAMPLE 13

To a mixture of 4-chlororesorcinol dimethyl ether (14.2 g), 2-fluorobenzoyl chloride (13.0 g) and 1,2-dichloroethane (200 ml) was added 11 g of aluminum chloride in small portions with ice-cooling and stirred. The agitation was continued at room temperature for 2 hours. After refluxing for 1 hour, the mixture was poured into iced water and extracted with ether. After washing with water and drying, the solvent was distilled off. To the residue, 32 g of 28% sodium methoxide (in methanol) and 300 ml of ethanol were added and the mixture was refluxed for 1 hour. After cooling the mixture, 200 ml of water was added and the solid crystal was recovered by filtration, washed with water and dried. The resulting crystal was added to a heated (185°–195° C.) pyridine hydrochloride and the mixture was stirred at that temperature for 2 hours. After cooling the mixture, water was added and the solid crystal was recovered by filtration, washed with water and dried. The resulting crystal was added into a mixture of potassium carbonate (22.6 g), ethyl bromoacetate (27.4 g) and DMF (400 ml) and the resulting mixture was stirred at 65°–75° C. for 2 hours. After cooling the mixture, sodium hydroxide (40 g) and water (400 ml) were added and the resulting mixture was stirred at 90°–100° C. for 1 hour. After cooling, the mixture was rendered acidic with hydrochloric acid and the solid crystal was recovered by filtration, washed with water and dried. Recrystallization from DMF gave 19 g of 2-chloro-9-oxo-9H-xanthene-3-yloxyacetic acid. m.p. 248°–249° C. This compound gave a mass spectrum having a molecular ion peak at m/e 304.

EXAMPLE 14

A mixture of 3-chloro-2-hydroxy-9-oxo-9H-xanthene (1.5 g), potassium carbonate (2.5 g), ethyl bromoacetate (3.1 g) and DMF (40 ml) was stirred at 65°–75° C. for 2 hours. After cooling the mixture, sodium hydroxide (4 g) and water (100 ml) were added and the resulting mixture was stirred at 90°–100° C. for 30 minutes. After cooling, the mixture was rendered acidic with hydrochloric acid and the solid crystal was recovered by filtration, washed with water and dried. Recrystallization from ethanol gave 1.5 g of 3-chloro-9-oxo-9H-xanthene-2-yloxyacetic acid. m.p. 237°–238° C. This compound showed a mass spectrum having a molecular ion peak at m/e 304.

EXAMPLE 15

A mixture of 4-bromo-2-hydroxy-9-oxo-9H-xanthene (2.0 g), potassium carbonate (1.9 g), ethyl bromoacetate (2.3 g) and DMF (20 ml) was stirred at 60°–70° C/ for 1.5 hours. After cooling the mixture, sodium hydroxide (4 g) and water (40 ml) were added and the resulting mixture was stirred at 90°–100° C. for 30 minutes. After cooling, the mixture was rendered acidic with hydrochloric acid and the solid crystal was recovered by filtration, washed with water and dried. Recrystallization from ethanol gave 1.8 g of 4-bromo-9-oxo-9H-xanthene-2-yloxyacetic acid. m.p. 219°–221° C. This compound exhibited a mass spectrum having a molecular ion peak at m/e 348.

EXAMPLE 16

A mixture of 1-chloro-3-hydroxy-9-oxo-9H-xanthene (1.0 g), potassium carbonate (1.1 g), ethyl bromoacetate (1.4 g) and DMF (20 ml) was stirred at 60°–70° C. for 5 hours. After cooling the mixture, sodium hydroxide (2 g) and water (50 ml) were added and the resulting mixture was stirred at 90°–100° C. for 30 minutes. After cooling, the mixture was rendered acidic with hydrochloric acid and the solid crystal was recovered by filtration, washed with water and dried. Recrystallization from ethanol gave 0.8 g of 1-chloro-9-oxo-9H-xanthene-3-yloxyacetic acid. m.p. 231°–233° C. This compound showed a mass spectrum having a molecular ion peak at m/e 304.

EXAMPLE 17

A mixture of 1,2-dichloro-3-hydroxy-9-oxo-9H-xanthene (2.0 g), potassium carbonate (2.0 g), ethyl bromoacetate (2.4 g) and DMF (40 ml) was stirred at 60°–70° C. for 1.5 hours. After cooling the mixture, sodium hydroxide (2 g) and water (100 ml) were added and the resulting mixture was stirred at 90°–100° C. for 30 minutes. After cooling, the mixture was rendered acidic with hydrochloric acid and the solid crystal was recovered by filtration, washed with water and dried. Recrystallization from DMF gave 1.7 g of 1.2-dichloro-9-oxo-9H-xanthene-3-yloxyacetic acid. m.p. 288°–290° C. This compound showed a mass spectrum having a molecular ion peak at m/e 338.

EXAMPLE 18

A mixture of 2-hydroxy-3-methyl-9-oxo-9H-xanthene (1.1 g), potassium carbonate (1.4 g), ethyl bromoacetate (1.7 g) and DMF (20 ml) was stirred at 60°–70° C. for 3 hours. After cooling the mixture, sodium hydroxide (4 g) and water (100 ml) were added and the resulting mixture was stirred at 90°–100° C. for 1 hour. After cooling, the mixture was rendered acidic with hydrochloric acid and the solid crystal was recovered by filtration, washed with water and dried. Recrystallization from DMF gave 1.3 g of 3-methyl-9-oxo-9H-xanthene-2-yloxyacetic acid. m.p. 225°–227° C. This compound showed a mass spectrum having a molecular ion peak at m/e 284.

EXAMPLE 19

A mixture of 3-hydroxy-1-methyl-9-oxo-9H-xanthene (5.0 g), potassium carbonate (6.0 g), ethyl bromoacetate (7.0 g) and DMF (100 ml) was stirred at 60°–70° C. for 5 hours. After cooling the mixture, sodium hydroxide (10 g) and water (200 ml) were added and the resulting mixture was stirred at 90°–100° C. for 1 hour. After cooling, the mixture was rendered acidic with hydrochloric acid and the solid crystal was recovered by filtration, washed with water and dried. Recrystallization from ethanol gave 5.0 g of 1-methyl-9-oxo-9H-xanthene-3-yloxyacetic acid. m.p. 189°–190°' C. This compound exhibited a mass spectrum having a molecular ion peak at m/e 284.

EXAMPLE 20

A mixture of 2-chloro-3-hydroxy-1-methyl-9-oxo-9H-xanthene (1.3 g), potassium carbonate (1.4 g), ethyl bromoacetate (1.7 g) and DMF (20 ml) was stirred at 60°–70° C. for 5 hours. After cooling the mixture, sodium hydroxide (4 g) and water (100 ml) were added and the resulting mixture was stirred at 90°–100° C. for 1 hour. After cooling, the mixture was rendered acidic with hydrochloric acid and the solid crystal was recovered by filtration, washed with water and dried. Recrystallization from DMF gave 0.9 g of 2-chloro-1-methyl-9-oxo-9H-xanthene-3-yloxyacetic acid. m.p. 275°–278° C. This compound showed a mass spectrum having a molecular ion peak at m/e 318.

EXAMPLE 21

A mixture of 2-bromo-3-hydroxy-9-oxo-9H-xanthene (5.0 g), potassium carbonate (7.1 g), ethyl bromoacetate (8.6 g) and DMF (80 ml) was stirred at 55°–65° C. for 5 hours. After cooling the mixture, sodium hydroxide (10 g) and water (250 ml) were added and the resulting mixture was stirred at 90°–100° C. for 2 hours. After cooling, the mixture was rendered acidic with hydrochloric acid and the solid crystal was recovered by filtration, washed with water and dried. Recrystallization from ethanol gave 3.0 g of 2-bromoto-9-oxo-9H-xanthene-3-yloxyacetic acid. m.p. 227°–230° C. This compound showed a mass spectrum having a molecular ion peak at m/e 348.

EXAMPLE 22

A mixture of 2,4-dichloro-3-hydroxy-9-oxo-9H-xanthene (7.5 g), potassium carbonate (7.5 g), ethyl bromoacetate (9.0 g) and DMF (100 ml) was stirred at 55°–65° C. for 3 hours. After cooling the mixture, sodium hydroxide (20 g) and water (250 ml) were added and the resulting mixture was stirred at 90°–100° C. for 1 hour. After cooling, the mixture was rendered acidic with hydrochloric acid and the solid crystal was recovered by filtration, washed with water and dried. Recrystallization from ethanol gave 4.0 g of 2,4-dichloro-9-oxo-9H-xanthene-3-yloxyacetic acid. m.p. 225°–228° C. This compound gave a mass spectrum having a molecular ion peak at m/e 338.

EXAMPLE 23

A mixture of 3-hydroxy-2-methyl-9-oxo-9H-xanthene (1.8 g), potassium carbonate (2.2 g), ethyl bromoacetate (2.7 g) and DMF (40 ml) was stirred at 60°–70° C. for 2 hours. After cooling the mixture, sodium hydroxide (3.2 g) and water (40 ml) were added and the resulting mixture was stirred at 90°–100° C. for 1 hour. After cooling, the mixture was rendered acidic with hydrochloric acid and the solid crystal was recovered by filtration, washed with water and dried. Recrystallization from ethanol gave 1.8 g of 2-methyl-9-oxo-9H-xanthene-3-yloxyacetic acid. m.p. 236°–238° C. This compound showed a mass spectrum having a molecular ion peak at m/e 284.

EXAMPLE 24

A mixture of 2-chloro-3-hydroxy-9-oxo-9H-xanthene (8.0 g), potassium carbonate (13 g), 2-bromoethanol (12 g) and DMF (200 ml) was stirred at 45°–55° C. for 3 hours. After distilling off the solvent under vacuum, water was added to the residue and the solid crystal was recovered by filtration, washed with water and dried. Recrystallization from a mixed solvent of DMF and water gave 6.0 g of 2-chloro-3-(2-hydroxyethoxy)-9-oxo-9H-xanthene. m.p. 153°–156° C. This compound produced a mass spectrum having a molecular ion peak at m/e 290.

EXAMPLE 25

To a mixture of 2-allyl-3-hydroxy-4-methyl-9-oxo-9H-xanthene (11 g) and chloroform (800 ml), 9.5 g of m-chloroperbenzoic acid was added and the resulting mixture was stirred at room temperature for 5 hours, followed by standing overnight. To the mixture, potassium carbonate (20 g) and water (500 ml) were added and the resulting mixture was subjected to extraction with chloroform. The chloroform layer was dried and the solvent was distilled off. The residue was recrystallized from ethanol to obtain 10 g of 2,3-dihydro-2-hydroxymethyl-11-methyl-5-oxo-5H-furo[3,2-b]xanthene. m.p. 242°–243° C. This compound gave a mass spectrum having a molecular ion peak at m/e 282.

EXAMPLE 26

To an ice-cooled mixture of 16.1 of the 2,3-dihydro-2-hydroxymethyl-11-methyl-5-oxo-5H-furo[3,2-b]xanthene obtained in Example 25 and 3,000 ml of acetone, a mixture of chromium trioxide (57 g), water (280 ml) and concentrated sulfuric acid (84 g) was added dropwise under agitation. The resulting mixture was left to stand overnight and filtered. The filtrate was evaporated to dryness under vacuum. After addition of water, the solid crystal was recovered by filtration, washed with water and dried. Recrystallization from a mixed solvent of methanol and dichloromethane gave 11.1 g of 2,3-dihydro-11-methyl-5-oxo-5H-furo[3,2-b]xanthene-2-carboxylic acid. m.p. 297°–299° C. This compound produced a mass spectrum having a molecular ion peak at m/e 296.

EXAMPLE 27

A mixture of 4-allyl-8-fluoro-3-hydroxy-9-oxo-9H-xanthene (1.4 g), m-chloroperbenzoic acid (1.2 g) and chloroform (250 ml) was stirred at room temperature for 5 hours and thereafter left to stand overnight. After addition of potassium carbonate (2 g) and water (50 ml), the mixture was extracted with chloroform. The chloroform layer was dried and the solvent was distilled off. The residue was recrystallized from ethanol to obtain 1.2 g of 7-fluoro-1,2-dihydro-2-hydroxymethyl-6-oxo-6H-furo[2,3-c]exanthene. m.p. 220°–221° C. This compound gave a mass spectrum having a molecular ion peak at m/e 286.

EXAMPLE 28

To an ice-cooled mixture of 8.0 g of the 7-fluoro-1,2-dihydro-2-hydroxymethyl-6-oxo-6H-furo[2,3-c]xanthene obtained in Example 27 and 1,000 ml of acetone, a mixture of chromium trioxide (14 g), water (80 ml) and concentrated sulfuric acid (24 g) was added dropwise under agitation. The resulting mixture was left to stand overnight and filtered. The filtrate was evaporated to dryness under vacuum. After addition of water, the solid crystal was recovered by filtration, washed with water and dried. Recrystallization from N,N-dimethylformamide (DMF) gave 8.1 g of 7-fluoro-1,2-dihydro-6-oxo-6H-furo[2,3-c]xanthene-2-carboxylic acid. m.p. 262°–265° C. This compound produced a mass spectrum having a molecular ion peak at m/e 300.

EXAMPLE 29

A mixture of 2-allyl-8-fluoro-3-hydroxy-4-methyl-9-oxo-9H-xanthene (9.0 g), m-chloroperbenzoic acid (8.0 g) and chloroform (1,000 ml) was stirred at room temperature for 5 hours and left to stand overnight. To the mixture, potassium carbonate (20 g) and water (500 ml) were added and the resulting mixture was extracted with chloroform. The chloroform layer was dried and the solvent was distilled off. The residue was dissolved in acetone (1,000 ml) and to the stirred solution, a mixture of chromium trioxide (21 g), water (120 ml) and concentrated sulfuric acid (36 g) was added dropwise at room temperature. After leaving it to stand overnight, the mixture was filtered and the filtrate was evaporated to dryness under vacuum. After addition of water, the solid crystal was recovered by filtration, washed with water and dried. Recrystallization from ethanol gave 5.0 g of 6-fluoro-2,3-dihydro-11-methyl-5-oxo-5H-furo[3,2-b]xanthene-2-carboxylic acid. m.p. 292°–295° C. This compound produced a mass spectrum having a molecular ion peak at m/e 314.

EXAMPLE 30

A mixture of 4-allyl-8-chloro-3-hydroxy-9-oxo-9H-xanthene (15 g), m-chloroperbenzoic acid (14 g) and chloroform (1,000 ml) was stirred at room temperature for 5 hours and left to stand overnight. To the mixture, potassium carbonate (20 g) and water (500 ml) were added and the resulting mixture was extracted with chloroform. The chloroform layer was dried and the solvent was distilled off. The residue was dissolved in acetone (2,000 ml) and, to the stirred solution, a mixture of chromium trioxide (15 g), water (90 ml) and concentrated sulfuric acid (26 g) was added dropwise at room temperature. After standing overnight, the mixture was filtered and the filtrate was evaporated to dryness under vacuum. After addition of water, the solid crystal was recovered by filtration, washed with water and dried. Recrystallization from ethanol gave 8.0 g of 7-chloro-1,2-dihydro-6-oxo-6H-furo[2,3-c]xanthene-2-carboxylic acid. m.p. 283°–286° C. This compound produced a mass spectrum having a molecular ion peak at m/e 316.

EXAMPLE 31

A mixture of 2-allyl-4,8-dichloro-3-hydroxy-9-oxo-9H-xanthene (14 g), m-chloroperbenzoic acid (11 g) and chloroform (1,000 ml) was stirred at room temperature for 5 hours and thereafter left to stand overnight. To the mixture, potassium carbonate (20 g) and water (500 ml) were added and the resulting mixture was extracted with chloroform. The chloroform layer was dried and the solvent was distilled off. The residue was dissolved in acetone (2,000 ml) and to the stirred solution, a mixture of chromium trioxide (17 g), water (100 ml) and concentrated sulfuric acid (30 g) was added dropwise at room temperature. After standing overnight, the mixture was filtered and the filtrate was evaporated to dryness under vacuum. After addition of water, the solid crystal was recovered by filtration, washed with water and dried. Recrystallization from ethanol gave 5.0 g of 6,11-dichloro-2,3-dihydro-5-oxo-5H-furo[3,2-b]xanthene-2-carboxylic acid. m.p. 291°–294° C. This compound showed a mass spectrum having a molecular ion peak at m/e 350.

EXAMPLE 32

A mixture of 4-allyl-3-hydroxy-9-oxo-9H-xanthene (10 g), m-chloroperbenzoic acid (21 g) and chloroform (1,000 ml) was stirred at room temperature for 5 hours and thereafter left to stand overnight. To the mixture, potassium carbonate (40 g) and water (1,000 ml) were added and the resulting mixture was extracted with chloroform. The chloroform layer was dried and the solvent was distilled off. The residue was dissolved in acetone (2,000 ml) and, to the stirred solution, a mixture of chromium trioxide (9 g), water (40 ml) and concentrated sulfuric acid (15 g) was added dropwise at room temperature. After standing overnight, the mixture was filtered and the filtrate was evaporated to dryness under vacuum. After addition of water, the solid crystal was recovered by filtration, washed with water and dried. Recrystallization from ethanol gave 4 g of 1,2-dihydro-6-oxo-6H-furo[2,3-c]xanthene-2-carboxylic acid. m.p. 283°–286° C. This compound showed a mass spectrum having a molecular ion peak at m/e 282.

EXAMPLE 33

A mixture of 2-allyl-4-chloro-3-hydroxy-9-oxo-9H-xanthene (2.0 g), m-chloroperbenzoic acid (3.6 g) and chloroform (100 ml) was stirred at room temperature for 5 hours and thereafter left to stand overnight. To the mixture, potassium carbonate (8 g) and water (200 ml) were added and the resulting mixture was extracted with chloroform. The chloroform layer was dried and the solvent was distilled off. The residue was dissolved in acetone (400 ml) and to the stirred solution, a mixture of chromium trioxide (1.7 g), water (10 ml) and concentrated sulfuric acid (3 g) was added dropwise at room temperature. After standing overnight, the mixture was filtered and the filtrate was evaporated to dryness under vacuum. After addition of water, the solid crystal was recovered by filtration, washed with water and dried. Recrystallization from ethanol gave 0.9 g of 11-chloro-2,3-dihydro-5-oxo-5H-furo[3,2-b]xanthene-2-carboxylic acid. m.p. 290°–293° C. This compound exhibited a mass spectrum having a molecular ion peak at m/e 316.

EXAMPLE 34

A mixture of 2-allyl-4-chloro-8-fluoro-3-hydroxy-9-oxo-9H-xanthene (2.8 g), m-chloroperbenzoic acid (4.7 g) and chloroform (100 ml) was stirred at room temperature for 5 hours and thereafter left to stand overnight. To the mixture, potassium carbonate (10 g) and water (200 ml) were added and the resulting mixture was extracted with chloroform. The chloroform layer was dried and the solvent was distilled off. The residue was dissolved in acetone (500 ml) and, to the stirred solution, a mixture of chromium trioxide (2.8 g), water (16 ml) and concentrated sulfuric acid (4.8 g) was added dropwise at room temperature. After standing overnight, the mixture was filtered and the filtrate was evaporated to dryness under vacuum. After addition of water, the solid crystal was recovered by filtration, washed with water and dried. Recrystallization from ethanol gave 1.0 g of 11-chloro-6-fluoro-2,3-dihydro-5-oxo-5H-furo[3,2-b]xanthene-2-carboxylic acid. m.p. 300° C. This compound showed a mass spectrum having a molecular ion peak at m/e 334.

EXAMPLE 35

A mixture of 4-allyl-2-chloro-3-hydroxy-9-oxo-9H-xanthene (2.9 g), m-chloroperbenzoic acid (3.5 g) and chloroform (300 ml) was stirred at room temperature for 5 hours and thereafter left to stand overnight. To the mixture, potassium carbonate (10 g) and water (200 ml) were added and the resulting mixture was extracted with chloroform. The chloroform layer was dried and the solvent was distilled off. The obtained 4-chloro-1,2-dihydro-2-hydroxymethyl-6-oxo-6H-furo[2,3-c]xanthene was dissolved in acetone (300 ml) and, to the stirred solution, a mixture of chromium trioxide (3.3 g), water (17 ml) and concentrated sulfuric acid (5 g) was added dropwise at room temperature. After standing overnight, to the mixture was added isopropanol (10 ml) and the resulting mixture was filtered and the filtrate was evaporated to dryness under vacuum. After adding water, the solid crystal was recovered by filtration, washed with water and dried. Recrystallization from ethanol gave 1.7 g of 4-chloro-1,2-dihydro-6-oxo-6H-furo[2,3-c]xanthene-2-carboxylic acid. m.p. 292°–295° C. This compound showed a mass spectrum having a molecular ion peak at m/e 316.

EXAMPLE 36

A mixture of 4-allyl-1-chloro-3-hydroxy-9-oxo-9H-xanthene (3.0 g), m-chloroperbenzoic acid (7.2 g) and chloroform (500 ml) was stirred at room temperature for 5 hours and thereafter left to stand overnight. To the mixture, potassium carbonate (20 g) and water (400 ml) were added and the resulting mixture was extracted with chloroform. The chloroform layer was dried and the solvent was distilled off. The residue was dissolved in acetone (300 ml) and, to the stirred solution, a mixture of chromium trioxide (3.3 g), water (17 ml) and concentrated sulfuric acid (5 g) was added dropwise at room temperature. After standing overnight, the mixture was filtered and the filtrate was evaporated to dryness under vacuum. After addition of water, the solid crystal was recovered by filtration, washed with water and dried. Recrystallization from ethanol gave 1.6 g of 5-chloro-1,2-dihydro-6-oxo-6H-furo[2,3-c]xanthene-2-carbolyxic acid. m.p. 255°–258° C. This compound showed a mass spectrum having a molecular ion peak at m/e 316.

EXAMPLE 37

A mixture of 4-allyl-3-hydroxyl-1-methyl-9-oxo-9H-xanthene (3.0 g), m-chloroperbenzoic acid (8 g) and chloroform (500 ml) was stirred at room temperature for 5 hours and thereafter left to stand overnight. To the mixture, potassium carbonate (20 g) and water (400 ml) were added and the resulting mixture was extracted with chloroform. The chloroform layer was dried and the solvent was distilled off. The residue was dissolved in acetone (500 ml) and, to the stirred solution, a mixture of chromium trioxide (5.5 g), water (25 ml) and concentrated sulfuric acid (8.5 g) was added dropwise at room temperature. After standing overnight, the mixture was filtered and the filtrate was evaporated to dryness under vacuum. After addition of water, the solid crystal was recovered by filtration, washed with water and dried. Recrystallization from ethanol gave 1.5 g of 1,2-dihydro-5-methyl-6-oxo-6H-furo[2,3-c]xanthene-2-carboxylic acid. m.p. 231°–234° C. This compound exhibited a mass spectrum having a molecular ion peak at m/e 298.

EXAMPLE 38

A mixture of 4-allyl-2-chloro-3-hydroxy-1-methyl-9-oxo-9H-xanthene (2.8 g), m-chloroperbenzoic acid (6.4 g) and chloroform (300 ml) was stirred at room temperature for 5 hours and thereafter left to stand overnight. To the mixture, potassium carbonate (20 g) and water (400 ml) were added and the resulting mixture was extracted with chloroform. The chloroform layer was dried and the solvent was distilled off. The residue was dissolved in acetone (500 ml) and, to the stirred solution, a mixture of chromium trioxide (5 g), water (25 ml) and concentrated sulfuric acid (8 g) was added dropwise at room temperature. After standing overnight, the mixture was filtered and the filtrate was evaporated to dryness under vacuum. After addition of water, the solid crystal was recovered by filtration, washed with water and dried. Recrystallization from ethanol gave 1.6 g of 4-chloro-1,2-dihydro-5-methyl-6-oxo-6H-furo[2,3-c]xanthene-2-carboxylic acid. m.p. 284°–287° C. This compound showed a mass spectrum having a molecular ion peak at m/e 330.

EXAMPLE 39

A mixture of 4-allyl-2-bromo-3-hydroxy-9-oxo-9H-xanthene (3.0 g), m-chloroperbenzoic acid (10 g) and chloroform (250 ml) was stirred at room temperature for 5 hours and thereafter left to stand overnight. To the mixture, potassium carbonate (20 g) and water (400 ml) were added and the resulting mixture was extracted with chloroform. The chloroform layer was dried and the solvent distilled off. The residue was dissolved in acetone (300 ml) and, to the stirred solution, a mixture of chromium trioxide (5 g), water (25 ml) and concentrated sulfuric acid (8 g) was added dropwise at room temperature. After standing overnight, the mixture was filtered and the filtrate was evaporated to dryness under vacuum. After addition of water, the solid crystal was recovered by filtration, washed with water and dried. Recrystallization from ethanol gave 1.5 g of 4-bromo-1,2-dihydro-6-oxo-6H-furo[2,3-c]xanthene-2-carboxylic acid. m.p. 283°–286° C. This compound showed a mass spectrum having a molecular ion peak at m/e 360.

EXAMPLE 40

A mixture of 4-allyl-3-hydroxy-2-methyl-9-oxo-9H-xanthene (12 g), m-chloroperbenzoic acid (12 g) and chloroform (700 ml) was stirred at room temperature for 5 hours and thereafter left to stand overnight. To the mixture, 20 g of potassium carbonate and 400 ml of water were added and the resulting mixture was extracted with chloroform. The chloroform layer was dried and the solvent was distilled off. The residue was dissolved in acetone (2,000 ml) and, to the stirred solution, a mixture of chromium trioxide (34 g), water (70 ml) and concentrated sulfuric acid (30 ml) was added dropwise at room temperature. After standing overnight, the mixture was filtered and the filtrate was evaporated to dryness under vacuum. After addition of water, the solid crystal was recovered by filtration, washed with water and dried. Recrystallization from a mixed solvent of ethanol and DMF gave 8.7 g of 1,2-dihydro-4-methyl-6-oxo-6H-furo[2,3-c]xanthene-2-carboxylic acid. m.p. 292°-295° C. This compound produced a mass spectrum having a molecular ion peak at m/e 296.

What is claimed is:

1. A xanthone derivative of the formula

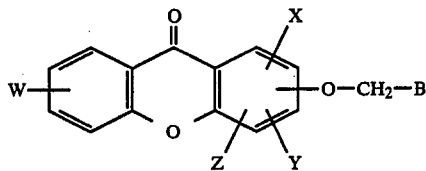

wherein W, X, Y and Z which are the same or different represent a hydrogen atom, a halogen atom or a lower alkyl group having 1 to 4 carbon atoms; B is a hydroxymethyl group, a lower alkoxycarbonyl group having 1 to 4 carbon atoms, or a carboxyl group, provided that a —O—CH$_2$—B group is bonded to the 2- or 3-position of the xanthone ring and that there is no case in which X, Y and Z are each a hydrogen atom concurrently; or a non-toxic salt of said derivative when B is a carboxyl group.

2. A compound according to claim 1, wherein at least one of X, Y and Z is selected from a halogen atom or an alkyl group having 1 to 4 carbon atoms.

3. A compound according to claim 1, wherein said alkyl group having 1 to 4 carbon atoms is methyl.

4. A compound according to claim 1, wherein said halogen atom is selected from chlorine or bromine.

5. A compound according to claim 1, wherein B is a carboxyl group.

6. A compound according to claim 2, wherein said alkyl group having 1 to 4 carbon atoms is methyl.

7. A compound according to claim 2, wherein said halogen atom is selected from chlorine or bromine.

8. A method for treating hypertension comprising administering to a patient suffering from hypertension an effective amount of a compound according to claim 1.

9. A method for treating hyperuricemia comprising administering to a patient suffering from hyperuricemia an effective amount of a compound according to claim 1.

* * * * *